United States Patent
Nicoud et al.

(12)

(10) Patent No.: US 6,409,923 B1
(45) Date of Patent: Jun. 25, 2002

(54) METHOD FOR ENRICHING OPTICAL ISOMERS BY MEANS OF SIMULATED MOBILE BED

(75) Inventors: Roger-Marc Nicoud, Lay Saint Christophe; Frédéric Charton, Nancy, both of (FR); Jean Blehaut, Swarthmore, PA (US)

(73) Assignee: Novasep S.A., Vandoeuvre-les-Nancy (FR)

( * ) Notice: Subject to any disclaimer, the term of this patent is extended or adjusted under 35 U.S.C. 154(b) by 0 days.

(21) Appl. No.: 09/646,466
(22) PCT Filed: Mar. 19, 1998
(86) PCT No.: PCT/FR98/00550
§ 371 (c)(1), (2), (4) Date: Sep. 19, 2000
(87) PCT Pub. No.: WO99/47228
PCT Pub. Date: Sep. 23, 1999
(51) Int. Cl.[7] ................................................. B01D 15/08
(52) U.S. Cl. ..................................... 210/659; 210/198.2
(58) Field of Search .................. 210/635, 656, 210/659, 662, 672, 198.2

(56) References Cited

U.S. PATENT DOCUMENTS

| | | | | |
|---|---|---|---|---|
| 4,498,991 A | | 2/1985 | Oroskar | 210/659 |
| 5,126,055 A | * | 6/1992 | Yamashita | 210/659 |
| 5,434,299 A | * | 7/1995 | Negawa | 210/659 |
| 5,498,752 A | * | 3/1996 | Negawa | 210/659 |
| 5,518,625 A | * | 5/1996 | Priegnitz | 210/659 |
| RE35,919 E | * | 10/1998 | Yamashita | 210/659 |
| 6,063,285 A | * | 5/2000 | Hotier | 210/659 |
| 6,136,198 A | * | 10/2000 | Adam | 210/198.2 |

FOREIGN PATENT DOCUMENTS

| | | | | |
|---|---|---|---|---|
| EP | 0 471 082 | | 2/1992 | 210/659 |
| WO | WO 91/08815 | | 6/1991 | 210/659 |

* cited by examiner

*Primary Examiner*—Ernest G. Therkorn
(74) *Attorney, Agent, or Firm*—Young & Thompson (57) ABSTRACT

The invention concerns a method for separating from a mixture two optical isomers using a simulated moving bed including an assembly of columns divided into at least three successive zones. The amount of charge injected is greater than that of the state of a predetermined reference state. The discharge flow is greater than that of the predetermined reference state if it is required at least to preserve the purity of the less immobilized enantiomer. The discharge flow is less than that of the reference state if it is required to preserve the purity of the more immobilized enantiomer.

11 Claims, 5 Drawing Sheets

METHOD FOR ENRICHING OPTICAL ISOMERS BY MEANS OF SIMULATED MOBILE BED

REFERENCE TO RELATED APPLICATIONS

This application is a 371 of PCT/FR98/00550 filed Mar. 19, 1998.

The present invention relates to a method intended for the separation of a mixture of two optical isomers, by means of a simulated mobile bed (SMB) using a chiral stationary phase and an achiral eluent.

It is known that, in chiral chromatography, porous solids are used with which a mixture of two optical isomers dissolved in a fluid, or a mixture of fluids, is placed in contact, which present different properties of adsorption having regard to each of the optical isomers. These porous solids are called chiral stationary phases or CSPs.

Most of the time, chiral chromatography methods employ a simple column, filled with chiral stationary phase, through which a fluid, called eluent, passes. At regular intervals of time, there is injected into the stream of eluent the mixture of the optical isomers to be separated, which is dissolved in an appropriate fluid, which may in particular be constituted by the eluent itself The mixture of optical isomers is thus entrained in the column and, at the outlet thereof, the optical isomer least adsorbed is, in known manner, recovered before the most adsorbed optical isomer.

In order to ensure separation of two optical isomers, it has also been proposed to employ a so-called "simulated mobile bed" technique. The simulated mobile bed is an old concept which has been used since the 1960s for the large-scale separation of the isomers of xylene, n-alkanes, iso-alkanes or fructose and glucose. Since 1990, it has been used in the domain of fine chemistry, and especially for the separation of optical isomers. Concerning this latter category of products, the simulated mobile bed is described as being an effective method for simultaneously obtaining two very pure optical isomers. Purities that may exceed 99.5% have thus been obtained. This technique has been described in particular in U.S. Pat. Nos. 2,985,589, 4,402,832, 4,498,991 and 5,126,055.

It is known that a simulated mobile bed is constituted by a given number of columns containing a stationary phase which are connected together in series. A solution, constituted by the mixture of the compounds to be separated dissolved in an appropriate fluid, called charge, and an eluent, are injected continuously at the inlet of two different columns. At the level of a column located downstream of the column where the charge is injected, a flux, called raffinate, is collected, which contains the enantiomer less immobilised in the eluent and, upstream of the column where the charge is injected, a flux, called discharge, is collected, which contains the enantiomer more immobilised in the eluent. In this way, a plurality of work zones are defined, each comprising a point of injection and a point of drawing-off.

The points of injection and of drawing-off are offset at regular intervals of time in the direction of flow. The interval of time located between two offsets of the points of injection/drawing-off is called a period.

Principally, two configurations of simulated mobile bed have been described: a simulated mobile bed with four zones and a simulated mobile bed with three zones (cf. Ruthven and Ching 1989 "Chemical Engineering Science").

A major drawback of this type of technique is that, beyond a given productivity, called maximum productivity of the installation, any increase in the amount of charge is made to the detriment of the purity of the products obtained, this limiting the development of the techniques of this type.

Applicants have established that it was possible to exceed the maximum productivity obtained in the simulated mobile beds functioning in accordance with the methods of the prior state of the art, while conserving the purity of one or the other of the separated enantiomers. In order to achieve such a result, Applicants have established that appropriate modifications of the functions exerted at the level of the different zones of the simulated mobile bed as well as of the flowrates employed were necessary.

The tests carried out by Applicants have thus led them to establish that, in order to improve the productivity of the installation, the amount of charge had, of course, to be increased but that, in order to obtain results likewise interesting from the standpoint of purity of the separated enantiomers, such increase had to be combined with an appropriate modification of the discharge flow.

The present invention thus has for its object to propose a method of separation of optical isomers which makes it possible to improve the yield of the methods according to the prior state of the art, while conserving the purity of one of the isomers obtained, and even by increasing the latter.

The present invention thus relates to a method of separation of a mixture of two optical isomers adapted to be more or less immobilised in a chiral stationary phase, this method being of the type employing a simulated mobile bed, constituted by an assembly of columns disposed in series, filled with a chiral stationary phase, which are divided into at least three successive zones, namely a first zone at the inlet of which an eluent is injected and at the outlet of which a flux, called discharge flux, principally containing the more immobilised enantiomer, is drawn off, a second zone at the inlet of which said mixture is injected, and a third zone at the outlet of which a flux, called raffinate flux, principally containing the less immobilized enantiomer is drawn off, characterized in that, with respect to a reference state in which: a) the optical isomer more immobilised in the stationary phase is completely desorbed in the first zone and is completely adsorbed in the third zone and where the optical isomer less immobilised in the stationary phase is completely desorbed in the second zone, and b) the amount of charge is maximum, the amount of charge injected is greater than that of the reference state, the discharge flow is greater than that of the reference state if it is desired at least to preserve the purity of the less immobilised enantiomer, or the discharge flow is less than that of the reference state if it is desired at least to preserve the purity of the more immobilised enantiomer.

In one form of embodiment of the invention, the amount of charge injected is rendered greater than that of the reference state by playing on the volumic flowrate of the charge.

In another form of embodiment of the invention, the amount of charge injected is rendered greater than that of the reference state by playing on the concentration of the charge.

Preferably, and as set forth in the form of embodiment described hereinafter, the simulated mobile bed comprises four zones, the fourth zone being located downstream of the point of drawing off of raffinate and, in the reference state, the optical isomer less immobilised in the stationary phase is completely adsorbed in this fourth zone. The outlet of the last zone is possibly connected to the inlet of the first zone.

Furthermore, it has been established that, at first approximation, the factor of increase of amount of charge, i.e. the ratio of the amount of charge injected according to the invention with respect to the amount of charge injected in the reference state, for narrow intervals of this factor, and the factor of correction of discharge flow, i.e. the ratio of the discharge flow with respect to the ratio of the discharge flow in the reference state, are bound by a substantially linear mathematical relationship. It will be noted that, under these conditions, the slope of the curve representing the variation of the factor of correction of discharge flow as a function of the variations of the factor of increase of amount of charge varies inversely with respect to the value of the selectivity of the stationary phase used.

More precisely, it has been established that the factor of increase of the amount of charge and the factor of correction of discharge flow are bound by a linear relationship expressing the ratio of the factor of increase of the amount of charge with respect to the factor of correction of discharge flow decreased by a value of one, as a function of the factor of correction of charge flow decreased by a value of one. It has also been established that the factor of proportionality of said linear relationship includes the value of the selectivity of the stationary phase used. More precisely, said factor of proportionality is substantially equal to a quarter of the value of the selectivity.

The present invention is applicable to a simulated mobile bed system constituted by a given number of columns disposed in series in zones allocated different functionalities. The mixture of the optical isomers that it is desired to separate and one or two achiral desorbents are continuously introduced in the columns containing an optically active stationary phase. Two streams containing the enriched optical isomers are extracted continuously from the line of columns. The charge and the desorbent or desorbents are injected via points of injection which are offset periodically in the direction of displacement of the eluent. The two flows of enriched optical isomers are recovered in periodically offset points of recovery.

A form of embodiment of the present invention will be described hereinafter by way of example, with reference to the accompanying drawings, in which:

DESCRIPTION OF PREFERRED EMBODIMENT

Figure 1:
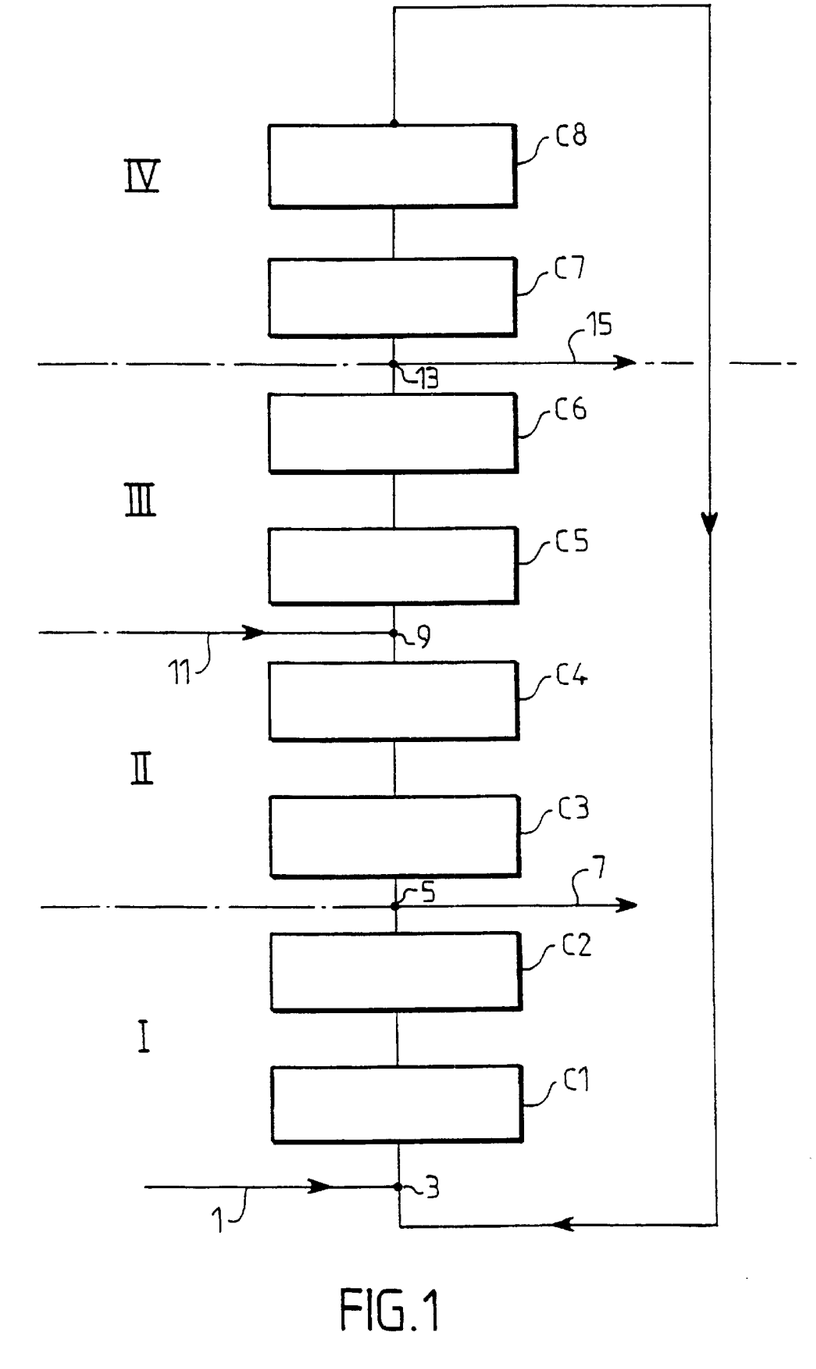
FIG. 1 is a schematic view of a series of columns constituting a simulated mobile bed enabling the method according to the invention to be carried out.

FIG. 1 shows by way of example an installation intended to ensure the separation of two optical isomers by means of a simulated mobile bed device, which is constituted in the present case by a series of eight columns $C_1, C_2, \ldots, C_8$ which are divided into four zones of two columns I, II, III, IV, these numberings being made in the direction of flow.

Zone I extends over the first two columns $C_1$ and $C_2$ between a point 3, where the eluent is injected via a conduit 1 and a point 5, where the most adsorbed optical isomer is drawn off, in the discharge flow via a conduit 7.

Zone II extends over columns $C_3$ and $C_4$ namely between the drawing off point 5 and a point 9 where the charge is continuously injected via a conduit 11, which charge is constituted by the mixture of the optical isomers which it is desired to separate which are dissolved in a diluent, which may in particular be constituted by the eluent injected at point 3.

Zone III extends over columns C5 and C6, namely between the point of injection 9 of the charge and a point 13 where the least adsorbed optical isomer is drawn off, in the flow of the raffinate via a conduit 15.

Zone IV extends over columns C7 and C8, namely between the drawing off point 13 of the raffinate and the point of injection 3 of the eluent. The outlet of column C8 is connected to the inlet of column C1.

In a functioning of conventional type, in simulated mobile bed for a chiral separation, flows $Q_I$, $Q_{II}$, $Q_{III}$ and $Q_{IV}$ in each of the respective zones I to IV are chosen in the following manner:

flow $Q_I$ is such that the more immobilised optical isomer is completely desorbed in zone I, flow $Q_{II}$ is such that the less immobilised optical isomer is completely desorbed in zone II, flow $Q_{III}$ is such that the more immobilised optical isomer is completely adsorbed in zone III, flow $Q_{IV}$ is such that the less immobilised optical isomer is completely adsorbed in zone IV.

The preceding conditions lead to several possible operational states. From these different possible states, the person skilled in the art can determine the one which leads to the highest productivity. This state will hereinafter be called "reference state".

Four examples of embodiment of the invention will be described hereinafter:

EXAMPLE I

In a first example of embodiment of the invention, it is proposed to separate by means of such a simulated mobile bed, the enantiomers of (+/−)-5-[1,2,3,4-tetrahydro-6-chinolyl]-6-methyl-3,6-dihydro-2H-1,3,4-thiadiazin-2-on which is dissolved in a solvent constituted by methanol at a concentration of 6 g/l. It was desired, during this operation, to collect the less immobilised enantiomer. To that end, a simulated mobile bed installation of the type described hereinabove was used, comprising eight columns divided into four work zones I, II, III, IV, as mentioned previously.

The stationary phase was a chiral phase of the tri (p-methyl) benzoate of cellulose type whose granulometry was from 20 to 45 micrometers. The diameter of each column was 26 mm and its length 10 cm. The eluent injected at point 3 was methanol. The temperature of the treatment was 25° C.

The starting point, or reference state, was determined by the conditions according to the prior state of the art in which a maximum of productivity is obtained. In this reference state, the flow of the charge injected at point 9 was 6.2 ml/min, the drawn off discharge flow at point 5 was 24.1 ml/min, the flow of drawn off raffinate at point 13 was 6.1 ml/min, the flow of eluent injected at point 3 was 24 ml/min, the flow $Q_1$ was 44.9 ml/min and the period was 14.6 min.

The purity of the less immobilised enantiomer which was drawn off at point 13, in the raffinate, was 99.2% (3 g/l) and the purity of the more immobilised enantiomer which was drawn off at point 5, from the discharge, was 98.2%. The productivity was 18.5 mg/min of less immobilised enantiomer.

According to the invention, the amount of charge injected at point 9 was increased to take it to a value of 9.3 ml/min, viz. a factor of increase of the amount of charge γ of 1.5, which was obtained by increasing the flow of the charge, and, correlatively, the discharge flow was increased by a factor of 1.2, hereinafter called factor of correction of discharge flow β. The purity and productivity of the enantiomer desired in the present case was measured, namely the less immobilised enantiomer. It was thus ascertained that 23.2 mg/min of this enantiomer with a purity of 99.5% was obtained.

Figure 2:
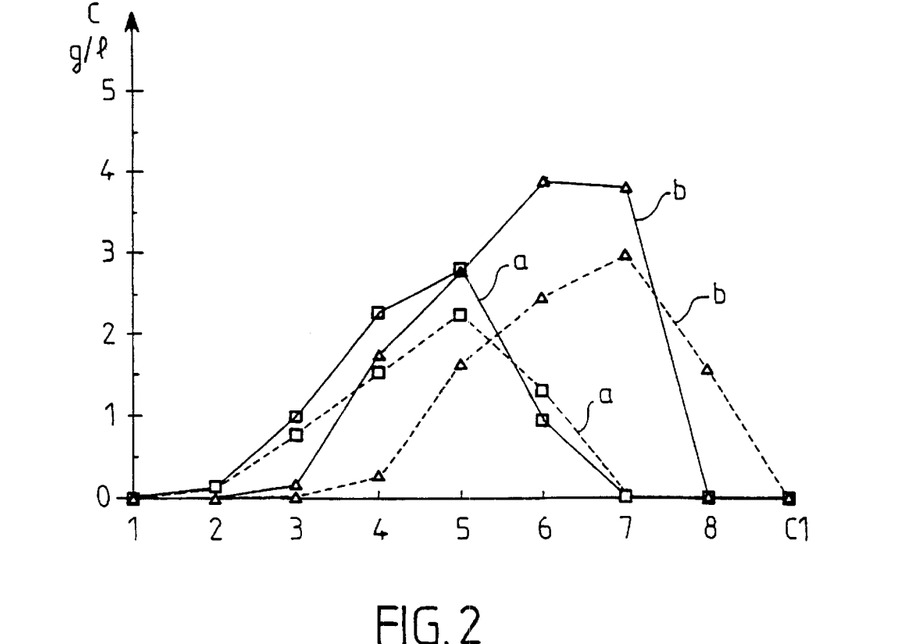
FIGS. 2 to 5 are graphs which show the concentration of more immobilised enantiomer (curves a) and of less immobilised enantiomers (curves b) at the inlet of each of the columns which constitute the simulated mobile bed, on the one hand in the case of a method according to the prior state of the art (curves in broken lines), in the case of the maximum possible productivity with this type of technique being attained, and, on the other hand, according to the invention (curves in solid lines), in the case of the productivity of the less immobilised enantiomer being increased.

FIG. 2 shows the curves of variation of the concentration C of more immobilised enantiomer (curve a) and of less immobilised enantiomer (curve b) in simulated mobile bed devices respectively according to the prior state of the art (curves in broken lines) and according to the invention (curves in solid lines), at the level of the inlet of each of the eight columns C1 to C8 of the device.

It is thus observed in FIG. 2 that, at the inlet of column C7, the concentration of more immobilised enantiomer is virtually zero, thus confirming the great purity obtained for the less immobilised enantiomer. It will also be noted that at the inlet of column C3, i.e. at the point of drawing off of the extract (the more immobilised enantiomer), the composition of less immobilised enantiomer according to the invention (curves in solid lines) is not zero as in the prior state of the art (curves in broken lines), which explains the reduced purity of the more immobilised enantiomer.

EXAMPLE II

A second example of embodiment of the invention will be described hereinafter, in which it is proposed to separate a racemic, namely binaphtol, which is dissolved in a solvent, which the the eluent used in the method, and which is constituted by an equivolume mixture of heptane and of isopropanol, the concentration of the charge thus constituted being 8 gl.

During this operation, it is desired to collect the less immobilised enantiomer. The method was carried out in a simulated mobile bed identical to that described previously.

Conditions of Implementation

| | |
|---|---|
| Racemic | Binaphtol |
| Selectivity | 1.45 |
| Diluent | Equivolume mixture of heptane and of isopropanol |

-continued

| | |
|---|---|
| Concentration of the racemic | 8 g/l |
| Nature of the eluent | Equivolume mixture of heptane and of isopropanol |
| Temperature of the treatment | 20° C. |
| Stationary phase | tri(3,5 dimethylphenyl carbamate) of amylose marketed under the Trademark "CHIRALPAK AD" |
| Sought enantiomer | The less immobilised one |

Reference State

| | |
|---|---|
| Flow of the charge injected at point 9 | 3.4 ml/min |
| Discharge flow drawn off at point 5 | 19.7 ml/min |
| Flow of raffinate drawn off at point 13 | 5.4 ml/min |
| Flow of eluent injected at point 3 | 21.7 ml/min |
| Flow in zone 1 | 70 ml/min |
| Period | 1.6 min |
| Composition of the flow of raffinate drawn off at point 13 | 98.6% of the less immobilised enantiomer |
| Productivity of the less immobilised enantiomer | 13.3 mg/min |

According to the invention, the amount of charge introduced at point 9 was multiplied by a factor of increase in amount of charge y equal to 3 and the amount of extract drawn off at point 5 was also increased.

The other operational conditions, namely the temperature of treatment, the flow of the raffinate drawn off at point 13, were preserved unchanged.

It has been observed that, under the conditions of the invention for operating the simulated mobile bed with an optimum yield, as the person skilled in the art knows how to do, the amount of extract injected had in that case to be multiplied by a factor of correction of discharge flow β, equal to 1.75.

Under these conditions, a productivity of the less immobilised enantiomer of 25 mg/min with a purity of 99.5% was obtained.

Figure 3:
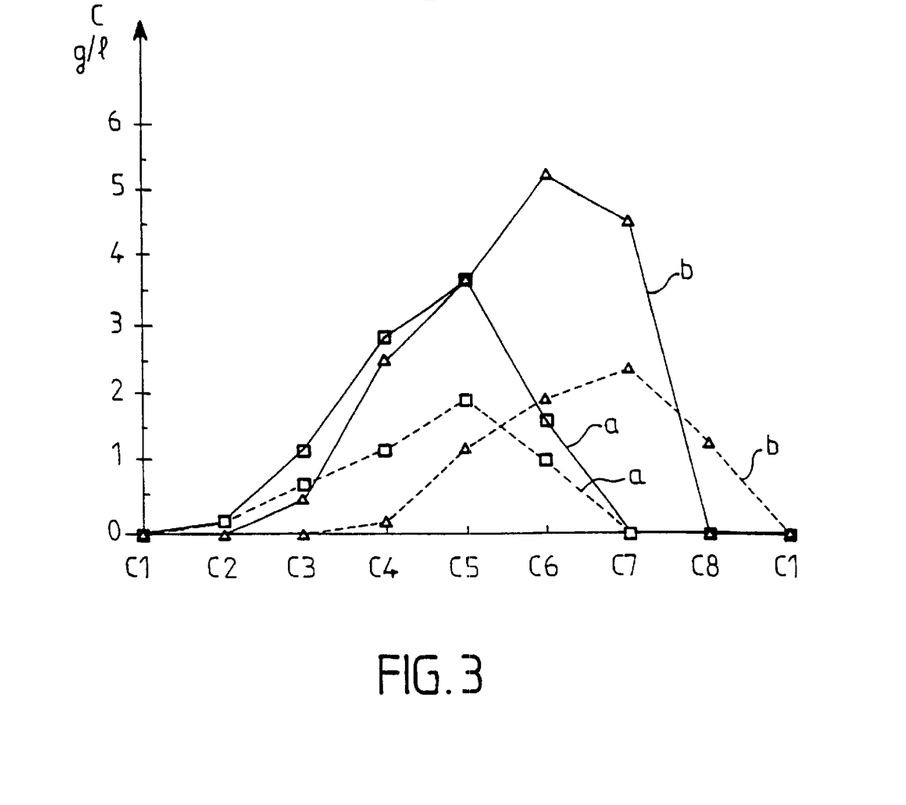

FIG. 3 shows the curves of variation in the concentration C of more immobilised enantiomer (curve a) and of less immobilised enantiomer (curve b) in simulated mobile bed devices respectively according to the prior state of the art (curves in broken lines) and according to the invention (curves in solid lines), at the level of the inlet of each of the eight columns C1 to C8 of the device.

It is thus ascertained that the present invention makes it possible to improve not only the productivity of one of the two enantiomers as desired, but also the purity thereof.

EXAMPLE III

A third example of embodiment of the invention will be described hereinafter in which it is proposed to effect the separation of a racemic ester.

Conditions of Implementation

| | |
|---|---|
| Racemic | Racemic ester |
| Selectivity | 1.3 |
| Diluent | n-heptane/isopropanol |
| Concentration of the racemic | 3 g/l |
| Nature of the eluent | n-heptane/isopropanol |
| Temperature of the treatment | 25° C. |

-continued

| | |
|---|---|
| Stationary phase | tri(p-methyl benzoate) of cellulose |
| Sought enantiomer | The less immobilised one |

Reference state

| | |
|---|---|
| Flow of the charge injected at point 9 | 4.3 ml/min |
| Discharge flow drawn off at point 5 | 15.1 ml/min |
| Flow of raffinate drawn off at point 13 | 5.6 ml/min |
| Flow of eluent injected at point 3 | 16.4 ml/min |
| Flow in zone 1 | 50 ml/min |
| Period | 9.6 min |
| Composition of the flow of raffinate drawn off at point 13 | 98.7% of the less immobilised enantiomer |
| Productivity of the less immobilised enantiomer | 6.3 mg/min |

According to the invention and, as previously, the amount of charge introduced at point 9 was multiplied by a factor of increase of amount of charge γ, equal to 1.3, and the amount of extract drawn off at point 5 was also increased.

The other operational conditions, namely the temperature of treatment, the flow of the raffinate drawn off at point 13, were preserved unchanged.

It was ascertained that, under the conditions of the invention for operating the simulated mobile bed with an optimum yield, as the person skilled in the art knows how to do, the amount of extract injected had in that case to be multiplied by a factor of correction of discharge flow β, equal to 1.20.

Under these conditions, a productivity of the less immobilised enantiomer of 8 mg/min with a purity of 98.9% was obtained, the purity in the extract of the more immobilised enantiomer being 95.1%.

Figure 4:
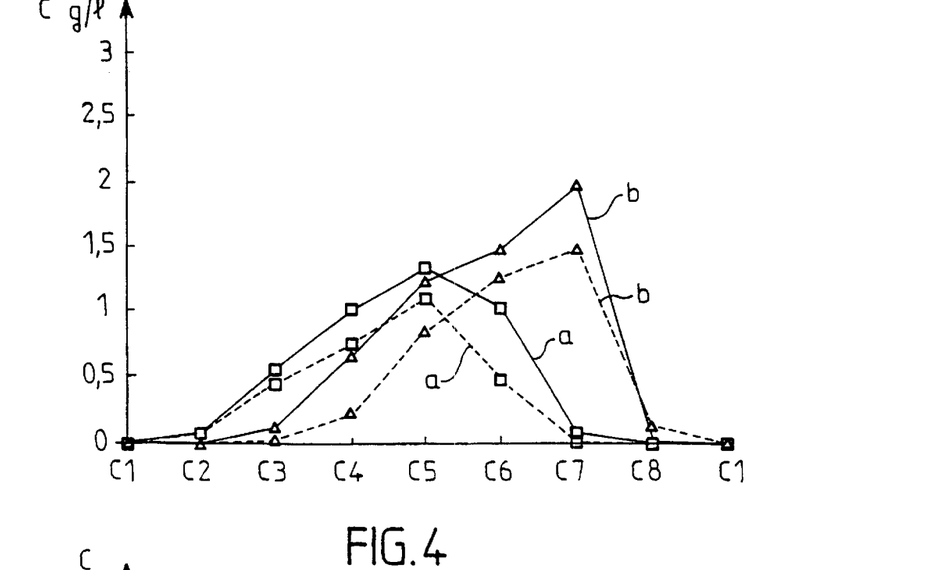

FIG. 4 shows the curves of variation in the concentration C of more immobilised enantiomer (curve a) and of less immobilised enantiomer (curve b) in simulated mobile bed devices respectively according to the prior state of the art (curves in broken lines) and according to the invention (curves in solid lines), at the level of the inlet of each of the eight columns C1 to C8 of the device.

EXAMPLE IV

In a fourth example of embodiment of the invention, the amount of charge introduced at point 9 was multiplied, from the same enantiomer and the same reference state as that of Example III, by a factor of increase of the amount of charge γ equal to 2, all the other operational parameters of the method remaining unchanged.

It was ascertained that, under the conditions of the invention for operating the simulated mobile bed with an optimum yield, as the person skilled in the art knows how to do, the amount of extract injected had in that case to be multiplied by a factor of correction of discharge flow β, equal to 1.5.

A productivity of the less immobilised enantiomer equal to 10.3 mg/min with a purity of 99.1% was obtained.

Figure 5:
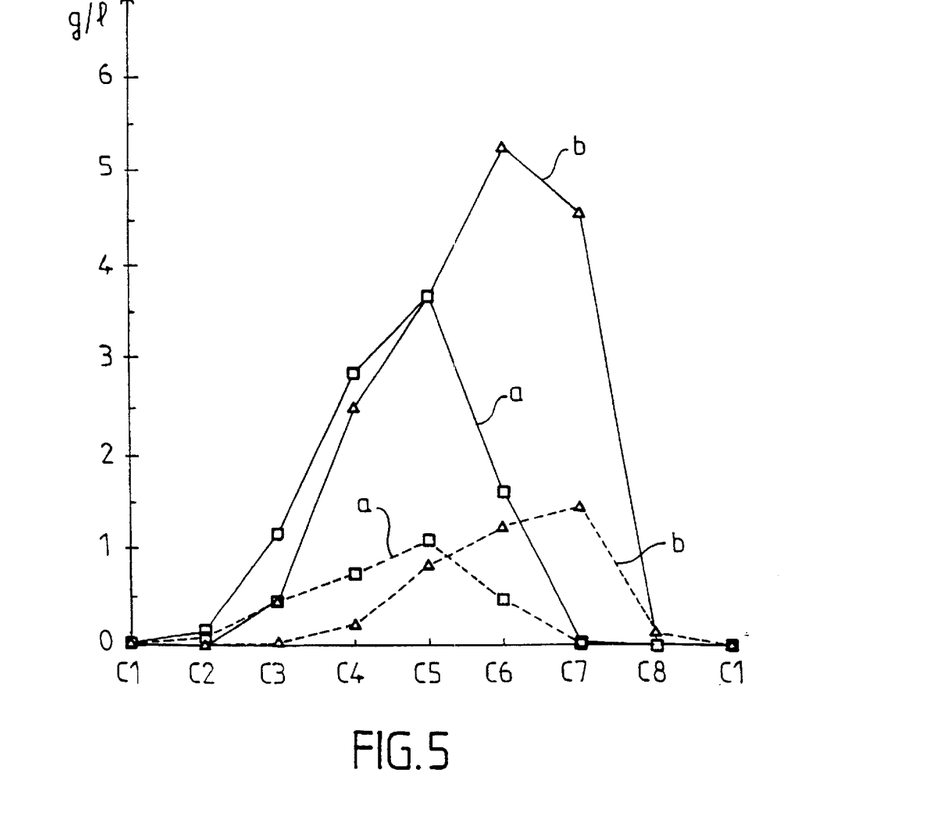

FIG. 5 shows the curves of variation in the concentration C of more immobilised enantiomer (curve a) and of less immobilised enantiomer (curve b) in simulated mobile bed devices respectively according to the prior state of the art (curves in broken lines) and according to the invention (curves in solid lines), at the level of the inlet of each of the eight columns C1 to C8 of the device.

In order to increase the amount of charge with respect to the reference state, one can play, as has been mentioned previously, on the flow of the charge by increasing said flow, but a charge flow identical to that of the reference state may equally well be conserved and the concentration of the charge increased.

All the experiments carried out by Applicants enabled them to ascertain, within the framework of the present invention, that the factor of correction of discharge flow β depended on the selectivity, i.e. a coefficient representative of the respective affinity of the two enantiomers for the stationary phase. It is known that the selectivity α is defined as follows:

$$\alpha = \frac{t2 - t0}{t1 - t0}$$

where:

$t_2$ is the time of retention of the more immobilised enantiomer $t_1$ is the time of retention of the less immobilised enantiomer $t_0$ to is the nonproductive time of the chromatography column in question, i.e. the time of passage of the fluid in the dead volume of the column.

Figure 6:
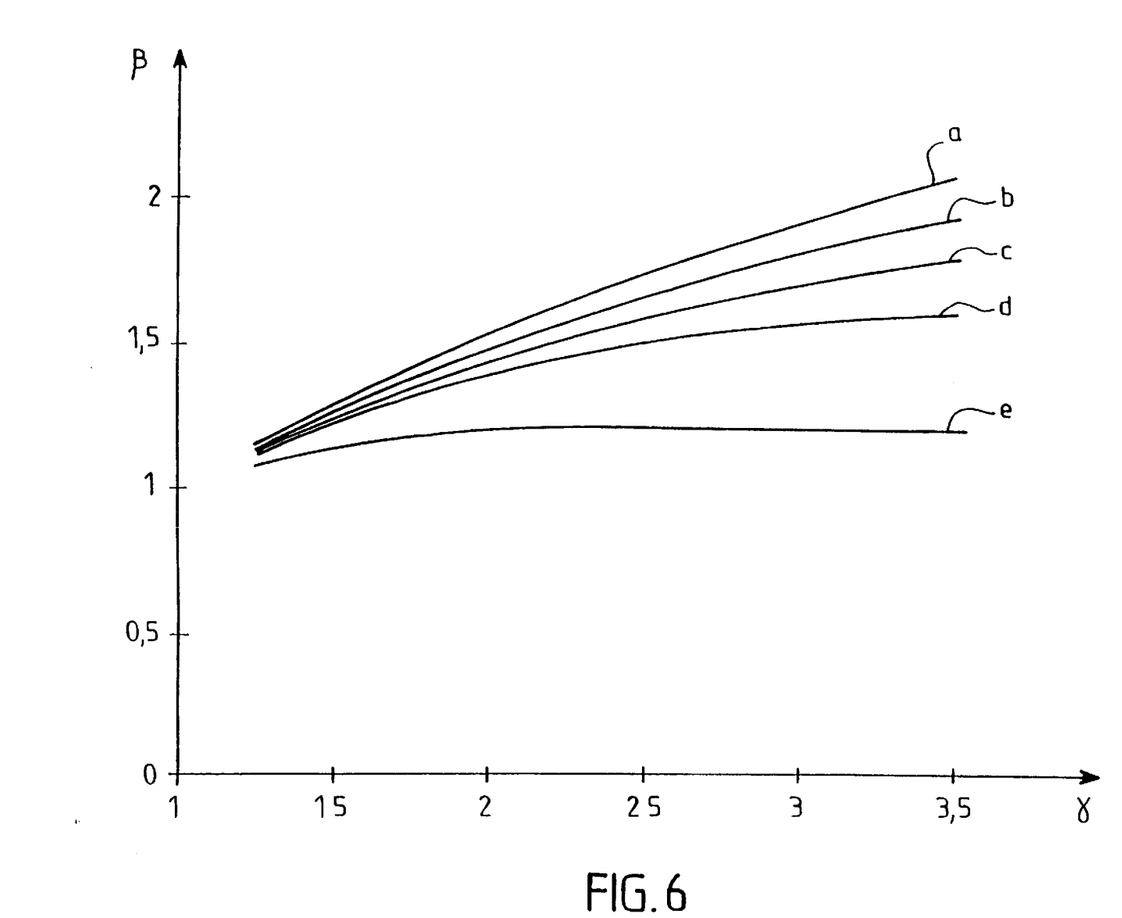
FIG. 6 is a graph representing the variation of the factor of correction of discharge flow as a function of the factor of increase of the amount of charge, for various values of the selectivity of the stationary phase.

The curves of variation of the factor of correction of discharge flow β, as a function of the factor of increase of the amount of charge γ for various values of the selectivity α and in particular for the values of the enantiomers studied, were established and shown in FIG. 6, namely:

| Curve Ref. | Enantiomer | Selectivity |
|---|---|---|
| a | Methyl 2-cyano-5-phenyl pentanoate | 1.1 |
| b | Racemic ester | 1.3 |
| c | Binaphtol | 1.4 |
| d | (+/−)-5-[1,2,3,4-tetrahydro-6-chinolyl]-6-methyl-3,6-dihydro-2H-1,3,4-thiadiazin-1-on | 1.8 |
| e | Methsuximide | 2.8 |

In a first approximation, in a relatively narrow range, for example for factors of increase of the amount of charge γ included between 2 and 3, it may be considered that the coefficients β and γ are bound by a substantially linear mathematical relationship. The slope of the curves α=f(γ) (represented in FIG. 6) thus varies approximately between 0.38 for a value of selectivity α of 1.1 to 0 for a value of selectivity α of 2.8.

Figure 7:
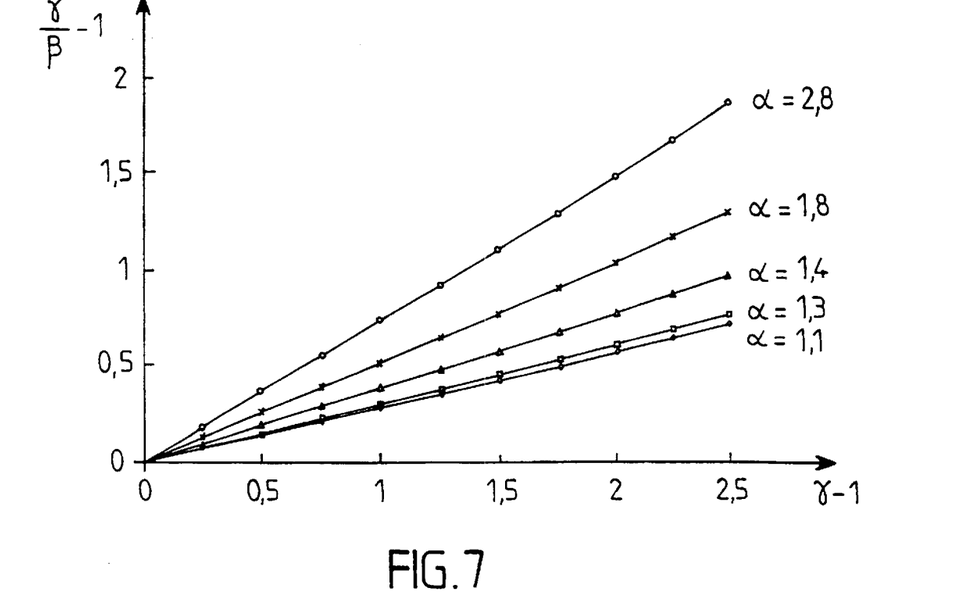
FIG. 7 is a graph representing the variation of the ratio of the factor of increase of the amount of charge with respect to the factor of correction of discharge flow decreased by a value of one, as a function of the factor of increase of the amount of charge decreased by a value of one, for five values of the selectivity of the stationary phase.
Figure 8:
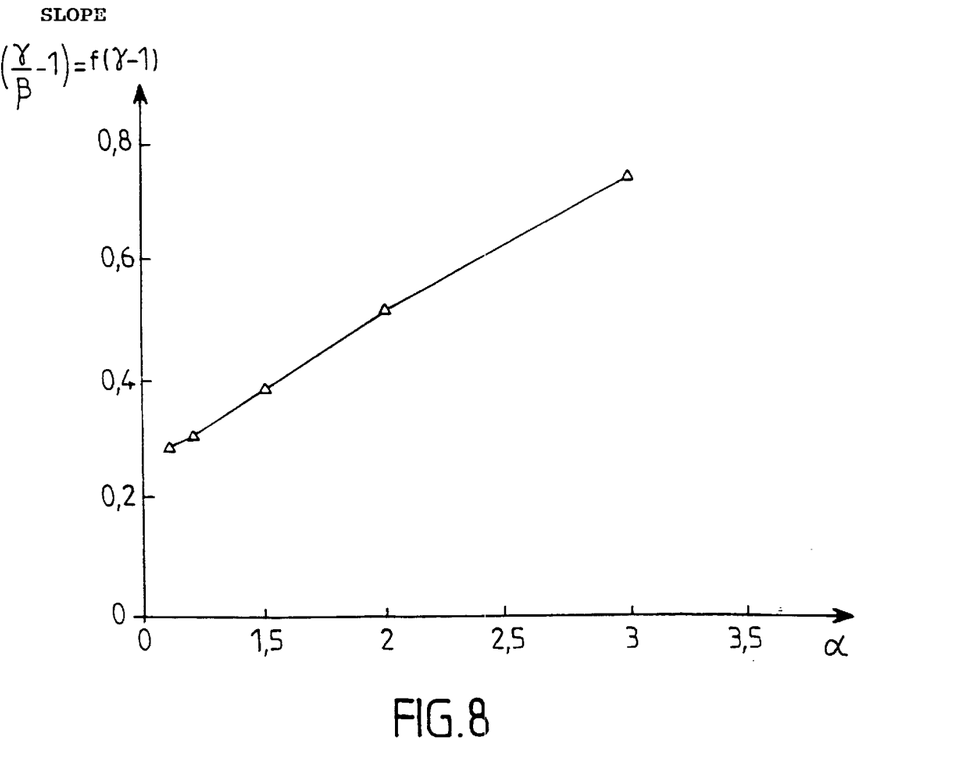
FIG. 8 is a graph representing the variation of the slope of the function represented in FIG. 7 as a function of the selectivity of the stationary phase.

More precisely, by the numerous tests that they made, Applicants established that the curve (FIG. 7) representing the variation of the ratio of the factor of increase of the amount of charge γ with respect to the factor of correction of the discharge flow α decreased by a value of one (viz the value γ/α−1) as a function of the factor of increase of the amount of charge γ minus one (viz the value γ−1) was a straight line. It was also established that the slope of this straight line depended on the value of the selectivity a of the stationary phase having regard to the two enantiomers in question. More precisely, it was established that this slope (as represented in FIG. 8) was substantially equal to a quarter of the selectivity α of the stationary phase (viz the value 0.25 α).

According to the invention, γ and β are thus substantially bound by the formula:

(γ/β−1)=0.25.α(γ−1)     (1)

The method according to the invention thus makes it possible to enrich two optical isomers constituted by a mixture of these isomers with a much improved productivity. In the majority of industrial methods of chiral separation, an optical isomer must be produced with a very high optical purity. Two principal cases of application may thus be defined:

in a first variant embodiment, the optical isomer which it is desired to produce is enriched to a purity less than that required. The step of enrichment according to the invention may be followed by an additional separation step such as a crystallization or an enantioselective resolution by simulated mobile bed with a chiral or achiral stationary phase, so that the overall treatment, namely the one according to the invention, completed by a subsequent treatment provides a result better than that of a one-step method such as a simulated mobile bed with a chiral stationary phase, in a second variant, the non-desired optical isomer is enriched to a purity less than that finally required.

The present invention may be followed by an additional treatment step, such as a racemization, making it possible to recycle a mixture of optical isomers in the method according to the invention from the enriched and non-desired optical isomer.

The present invention may, of course, also be carried out when it is desired to increase the productivity and purity of the more immobilised enantiomer. The modus operandi would in that case be the same as previously, except that, in that case, the amount of extract would be decreased by dividing it by the factor of correction of discharge flow $\beta$.

Although the present invention has been described having regard to applications developed with simulated mobile bed devices with four zones, the person skilled in the art will, of course, be able to apply the teaching of the present invention to other models of simulated mobile beds such as in particular devices with three zones.

What is claimed is:

1. Method of separation of a mixture of two optical isomers adapted to be more or less immobilised in a chiral stationary phase, this method being of the type employing a simulated mobile bed, constituted by an assembly of columns (C1, C2, C3, C4, C5, C6, C7, C8) disposed in series, filled with a chiral stationary phase, which are divided into at least three successive zones (I, II, III), namely a first zone (I) at the inlet of which an eluent is injected and at the outlet of which a flux, called discharge flux, principally containing the more immobilised enantiomer, is drawn off, a second zone (II) at the outlet of which said mixture is injected, and a third zone (III) at the outlet of which a flux, called raffinate flux, principally containing the less immobilized enantiomer is drawn off, characterized in that, with respect to a reference state in which: a) the optical isomer more immobilised in the stationary phase is completely desorbed in the first zone (I) and is completely adsorbed in the third zone (III) and where the optical isomer less immobilised in the stationary phase is completely desorbed in the second zone (II), and b) the amount of charge is maximum, the amount of charge injected is greater than that of the reference state, the discharge flow is greater than that of the reference state if it is desired at least to preserve the purity of the less immobilised enantiomer, or the discharge flow is less than that of the reference state if it is desired at least to preserve the purity of the more immobilised enantiomer.

2. Method according to claim 1, characterized in that the amount of charge injected is rendered greater than that of the reference state by playing on the volume flow of the charge.

3. Method according to claim 1, characterized in that the amount of charge injected is rendered greater than that of the reference state by playing on the concentration of the charge.

4. Method according to claim 1, characterized in that a simulated mobile bed comprising four zones (I, II, III, IV) is used, the fourth zone (IV) being located downstream of the drawing-off point (13) of raffinate and, in the reference state, the less immobilised optical isomer in the stationary phase is completely adsorbed in this fourth zone (IV).

5. Method according to claim 1, characterized in that the outlet of the last zone is connected to the inlet of the first zone.

6. Method according to claim 1, characterized in that, at first approximation, the factor of increase of amount of charge ($\gamma$), i.e. the ratio of the amount of charge injected with respect to the amount of charge injected in the reference state, for narrow intervals of this factor, and the factor of correction of discharge flow ($\beta$), i.e. the ratio of the discharge flow with respect to the ratio of the discharge flow in the reference state, are bound by a substantially linear mathematical relationship.

7. Method according to claim 6, characterized in that the slope of the curve representing the variation of the factor of correction of the discharge flow ($\beta$) as a function of the variation of the factor of increase of amount of charge ($\gamma$) varies inversely with respect to the value of the selectivity ($\alpha$) of the stationary phase used.

8. Method according to claim 1, characterized in that the factor of increase of the amount of charge ($\gamma$) and the factor of correction of discharge flow ($\beta$) are bound by a linear relationship expressing the ratio of the factor of increase of the amount of charge with respect to the factor of correction of discharge flow ($\gamma/\beta$) decreased by a value of one ($\gamma/\beta-1$), as a function of the factor of correction of charge flow ($\gamma$) decreased by a value of one.

9. Method according to claim 8, characterized in that the factor of proportionality of said linear relationship comprises the value of the selectivity ($\alpha$) of the stationary phase used.

10. Method according to claim 9, characterized in that said factor of proportionality is substantially equal to a quarter of the value of the selectivity ($\alpha$).

11. Method according to one of claims 8 to 10, characterized in that the factor of increase of the amount of charge ($\gamma$), the factor of correction of discharge flow ($\beta$) and the selectivity ($\alpha$) are substantially bound by the relationship:

$$(\gamma/\beta-1)=0.25.\alpha(\gamma-1).$$

* * * * *